(12) United States Patent
Gawlik

(10) Patent No.: US 6,477,851 B1
(45) Date of Patent: Nov. 12, 2002

(54) ANALYSIS GAS-COOLING DEVICE

(75) Inventor: Helmut Gawlik, Ratingen (DE)

(73) Assignee: M & C Products Analysentechnik GmbH (DE)

( * ) Notice: Subject to any disclaimer, the term of this patent is extended or adjusted under 35 U.S.C. 154(b) by 0 days.

(21) Appl. No.: 09/721,073

(22) Filed: Nov. 22, 2000

(30) Foreign Application Priority Data

Nov. 27, 1999 (DE) .......................................... 199 57 052

(51) Int. Cl.⁷ ............................................... F25B 41/04
(52) U.S. Cl. ........................................................ 62/217
(58) Field of Search ........................... 62/217, 474, 511

(56) References Cited

U.S. PATENT DOCUMENTS

| | | | | |
|---|---|---|---|---|
| 3,040,544 A | * | 6/1962 | Atchison | 62/217 X |
| 3,882,691 A | * | 5/1975 | Baines et al. | 62/217 X |
| 3,914,952 A | * | 10/1975 | Barbier | 62/217 X |
| 4,389,855 A | * | 6/1983 | Ueda et al. | 62/217 X |
| 6,076,368 A | * | 6/2000 | Noble | 62/217 |

FOREIGN PATENT DOCUMENTS

| | | |
|---|---|---|
| AT | 7004376 | 8/1970 |
| DE | 3188321 A1 | 12/1989 |
| DE | 19817372 C1 | 10/1999 |

* cited by examiner

Primary Examiner—Harry B. Tanner
(74) Attorney, Agent, or Firm—Mark Kusner; Michael A. Jaffe

(57) ABSTRACT

The invention relates to an analysis gas-cooling device with a circuit for a cooling agent, which flows through a compressor, a liquefier, and an evaporator.

10 Claims, 1 Drawing Sheet

ANALYSIS GAS-COOLING DEVICE

DESCRIPTION

Figure 1:
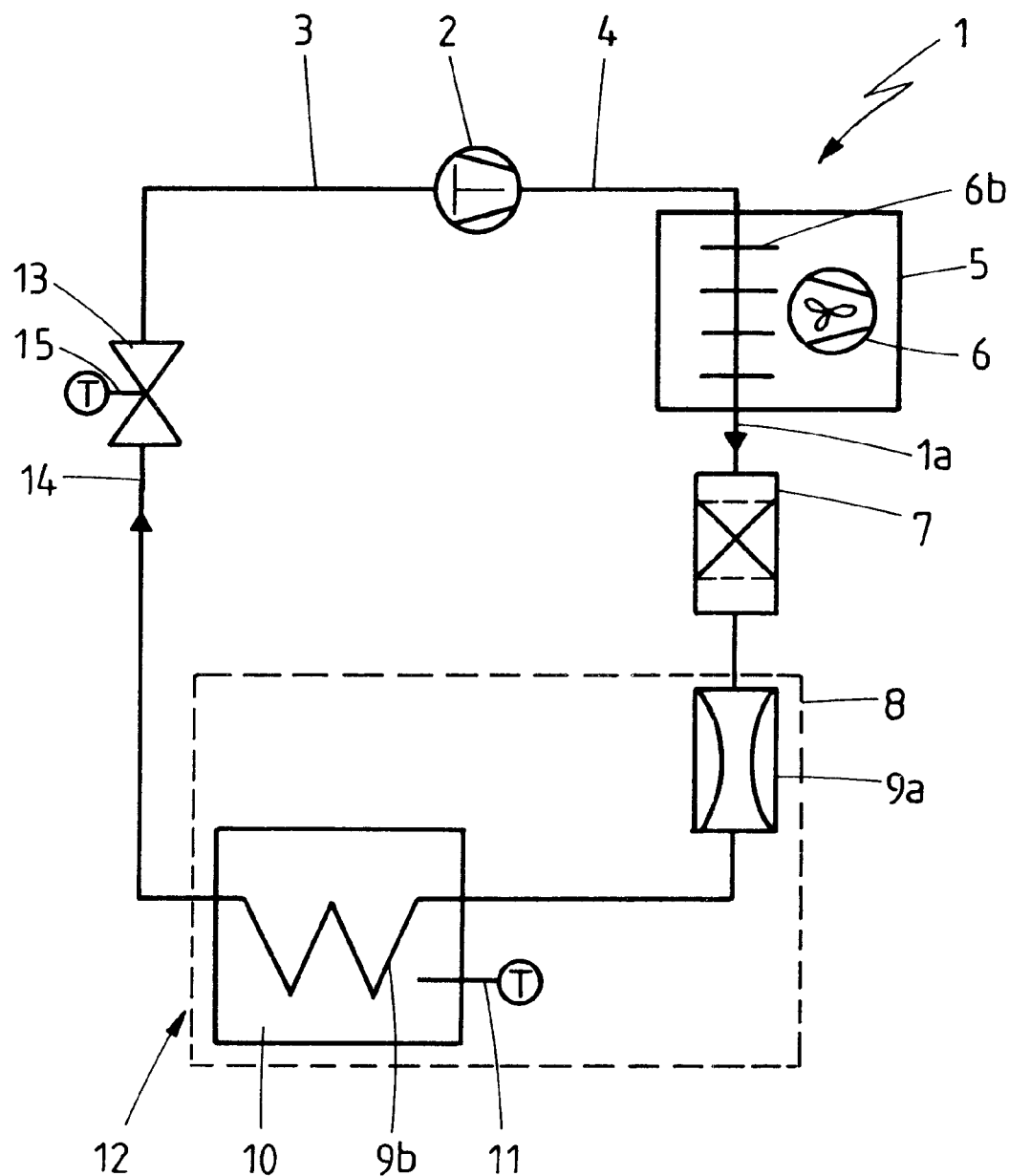

The invention relates to an analysis gas-cooling device.

Such devices are used for the cooling of gas samples which are to be analyzed and which are to be kept at a constant temperature for their analysis. This is important, for example, in order to be able to adjust the dew point of the analysis gas, i.e. the temperature at which the partial pressure of the water vapour contained in it is equal to its saturation vapour pressure. For this purpose, the cooling agent of the cooling device is to be kept at a temperature which is to be maintained as exactly constant as possible. This temperature lies typically in the range between 0 and 10° C. The regulating increment in the prior art was, for example, +/−1.0° C. Because the gases to be analyzed are only examined in samples of low volume, the cooling device requires only a low cooling capacity, for example in the range of 100 Watts or less.

The analysis gas is connected to the cooling device by, for example, cooling hoses, which are intended to be kept at a constant temperature by the cooling device, in the manner of a heat exchanger.

To effect the maintaining of a constant temperature, the principle is known of switching a compressor included in the cooling circuit on or off under temperature regulation. By switching the compressor off when a lower limit temperature is reached, the feed of the initially fluidised cooling agent to an evaporator is stopped, so that no further heat extraction can take place due to the change of state of the aggregate of the cooling agent in the evaporator, and the temperature measured at that point rises accordingly. Once an upper limit temperature is reached, the compressor is switched on again, in order to bring about the regulating of the temperature downwards once again, and reducing the temperature of the analysis gas. This incurs a high degree of wear of the compressor, and, in addition, the precision of such a regulating system is low, since even with the compressor switched off there will initially still be cooling agent injected into the evaporator.

The invention is based on the problem of achieving an improvement in this.

The basic philosophy of the invention is to measure the temperature at the cooling device continually or cyclically, and, as a function of fluctuations in relation to a specified reference value, to adjust the inflow of the cooling agent to a conveying device (compressor) for the cooling agent correspondingly.

To achieve this, the invention proposes, in its most general embodiment, an analysis gas-cooling device with a circuit for a cooling agent, whereby the circuit comprises at least one compressor, a liquefier (condenser) downstream of this, and an evaporator for the cooling agent connected to the compressor on the output side, whereby a control element is connected between the output side of the evaporator and the compressor, so as to influence the gas flow conducted from the evaporator to the compressor.

By means of the arrangement according to the invention of a control element between the output side of the evaporator and the compressor, the regulating of the temperature is possible solely by influencing this control element. The compressor, as a conveying device, can continue to run throughout, unaffected by this, without being subjected to the switching procedures which incur wear.

The control element can be incorporated in a control circuit and can be actuated by a temperature as an input parameter, measured at the evaporator. This means that an external influence of the cooling device becomes superfluous, the temperature will automatically be kept constant.

If a valve is used as the control element, a cheap and reliable component is provided which takes charge of the interruption or passing respectively of the gas flow between the evaporator and the compressor.

In this situation, the control element can reduce or shut off the gas flow between the evaporator and the compressor if a lower limit temperature is undercut, and, respectively, if an upper limit temperature is exceeded, it can increase the gas flow between the evaporator and the compressor, up to a maximum value.

Accordingly, the valve can throttle the gas flow in whole or in part, or respectively allow it clear passage.

In order to remove any residual water which may be present in the cooling agent, a drying unit for the cooling agent can be connected upstream of the evaporator.

Further advantages and features can be derived from an embodiment of the object of the invention represented in the drawing and described hereinafter.

The drawing shows:

FIG. 1: A schematic circuit diagram of an analysis gas-cooling device according to the invention.

According to the embodiment, the analysis gas-ooling device, designated in its entirety by 1, comprises in a circuit 1a a compressor 2, which compresses a gas being conveyed at the input side (at 3), which features a pressure in the range from about 0 to 1 bar, up to a pressure of about 10 to 15 bar at the output side (at 4).

The gas which is compressed in this way is conducted to a liquefier 5, which effects the cooling of the gas being conducted through it by means of a cooling blower 6, for which purpose cooling ribs 6b can be provided so as to increase the area of impingement.

As a result of the cooling on the one hand and the increase in pressure on the other, fluidisation takes place of the gas being passed through, which can be conducted to a dryer 7, optionally arranged further on in the circuit 1, which carried out water separation by means of chemical or physical absorption.

The fluidised cooling agent is then conducted to a unit designated overall by 8.

The cooling agent is in this situation guided initially through a capillary tube 9a, whereby the pressure of the cooling agent is reduced, for example to 1–2 bar. It then passes into an evaporator 9b, which is located in a cooling block 10, which is cooled via the evaporator 9b.

Arranged in the cooling block 10 is a heat exchanger (not shown), through which the gas which is to be analyzed is conducted.

Temperature compensation accordingly takes place between the evaporator 9b and the heat exchanger referred to.

The cooling agent does not come in contact with the heat exchanger. No exchange takes place between the analysis gas and the cooling agent circuit 1a.

In the evaporator 9b, the change in the state of the aggregate of the cooling agent, from fluid to gaseous, causes the evaporation heat to be drawn off, which is required in order to effect the change of state of the aggregate. This causes the analysis gas to be cooled.

In the cooling block 10 the temperature T is measured by a measurement sensor 11, whereby the measurement can be effected constantly or cyclically. At the output (at 12) of the evaporator 9b the cooling agent is conducted to a control element 13, which exerts an influence on the gas volume flow between the evaporator 9b and the input side 3 of the compressor 2.

In the embodiment shown, the control element 13 is designed as a valve, which allows either for complete opening or blocking of the cooling agent being conducted in a line 14. In principle, consideration can also be given to control elements 13 with continuous or graduated variable intermediate opening states.

In the embodiment shown, the cooling device 1 is designed overall as a control circuit, whereby the temperature acquired by the measuring sensor 11 in the cooling block 10 forms an input signal 15 for the control element 13.

During operation, on attaining an upper limit temperature, measured at the temperature sensor 11, the valve 13 is switched to throughflow. This causes new cooling agent to flow into the evaporator 9b, where it is evaporated and draws heat from the surrounding area, so that the temperature in the evaporator drops, as a result of which the analysis gas is also obstructed accordingly from exceeding a limit temperature.

If the temperature drops further, at a lower limit temperature the measuring sensor 11 issues a signal to the input 15 of the valve, which has the effect of blocking the flow of the cooling agent through this valve 13. Despite the continued operation of the compressor 2, it cannot deliver any cooling agent into the circuit because of the lack of gas being delivered on the input side 3, with the result that no further cooling agent can be evaporated at the evaporator 9b, and accordingly no further energy extraction from the surroundings and from the analysis gas takes place. The temperature of the analysis gas therefore rises again, which finally, on the attainment of an upper limit temperature, acquired by the measuring sensor 11, leads to the opening of the valve 13 again. The renewed feed of cooling agent into the evaporator 8 then again causes the temperature of the analysis gas to drop.

A cooling device 1 of this kind, according to the invention, can effect a very precise temperature regulation in the range of +/−0.1° C.

The cooling device according to the invention works independently of the ambient temperature, and takes account solely of the temperature acquired at the measuring sensor 11 in the cooling block 10, or in its constituent parts respectively. This regulation is also independent of the power absorbed.

What is claimed is:

1. An analysis gas-cooling device (1) with a circuit (1a) for a cooling agent, whereby the circuit (1a) comprises at least one compressor (2), a liquefier (5) downstream of this, and an evaporator (9b) for the cooling agent connected to the compressor (2) for analysis gas-cooling, characterised in that a control element (13) is arranged between an output side (12) of the evaporator (9b) and an input side of the compressor (2), so as to influence the gas flow conducted from the evaporator (9b) to the compressor (2), wherein said control element is a switching element that is capable of being actuated in a throughflow direction allowing complete flow of the cooling agent therethrough, and in a blocking direction, completely blocking flow of the cooling agent therethrough.

2. The analysis gas-cooling device according to claim 1, characterised in that the circuit (1a) is designed as a control circuit.

3. The analysis gas-cooling device according to claim 2, characterised in that the regulating is effected as a function of a measured temperature (T).

4. The analysis gas-cooling device according to claim 3, characterised in that the temperature (T) at the evaporator (9b) is capable of being measured and can be transferred as an input signal (15) to the control element (13).

5. The analysis gas-cooling device according to claim 3, characterised in that, in the event of a lower limit temperature being undercut, the control element (13) reduces the gas flow between the evaporator (9b) and the compressor (2).

6. The analysis gas-cooling device according to claim 3, characterised in that, in the event of an upper limit temperature being exceeded, the control element (13) increases the gas flow between the evaporator (9b) and the compressor (2).

7. The analysis gas-cooling device according to claim 1, characterised in that the switching element (13) is a valve.

8. The analysis gas-cooling device according to claim 1, characterised in that a drying unit (7) for the cooling agent is arranged upstream of the evaporator (9b).

9. The analysis gas-cooling device according to claim 1, characterised in that a capillary device (9a) in a circuit (1a) is arranged upstream of the evaporator (9b).

10. The analysis gas-cooling device according to claim 1, characterised in that the evaporator (9b) is arranged in or around a cooling block (10), through which the analysis gas can be conducted.

\* \* \* \* \*